United States Patent [19]

Spaulding

[11] Patent Number: 4,782,725

[45] Date of Patent: Nov. 8, 1988

[54] ARTICLE IDENTIFICATION DEVICE

[75] Inventor: Darwin Spaulding, Voorheesville, N.Y..

[73] Assignee: Spaulding & Rogers Mfg., Inc., N.Y.

[21] Appl. No.: 83,700

[22] Filed: Aug. 7, 1987

[51] Int. Cl.$^4$ ................................................ B43K 5/00
[52] U.S. Cl. ........................................ 81/9.22; 30/362
[58] Field of Search ................ 81/9.22; 128/329, 253, 128/316, 303 R, 76.5, 1 R, 355; 30/366, 362; 604/22, 46, 47; 132/88.7

[56] References Cited

U.S. PATENT DOCUMENTS

| 917,146 | 4/1909 | Ramsay et al. | 30/362 |
| 4,159,659 | 7/1979 | Nightingale | 81/9.22 |
| 4,204,438 | 5/1980 | Binaras et al. | 81/9.22 |

Primary Examiner—Roscoe V. Parker
Attorney, Agent, or Firm—McGlew and Tuttle

[57] ABSTRACT

An identification device including a device body, a drive unit housed in the device body, a sliding dovetail shaped armature with a horizontal slot, a needle bar which is inserted into the armature and is secured by means of a spring loaded ball and screw. The armature moves in a vertical direction by means of its connection with a circular rotor attached to the drive unit. The rotor has at its rear end an offset pin which engages the horizontal slot located at the upper front portion of the armature, wherein the rotational movement of the circular rotor is translated into vertical motion of the sliding dovetail armature which assures that therre will be no horizontal displacement of the needle bar and thus achieving precise columnation of the needle bar and therefore precise application of the identification ink.

18 Claims, 7 Drawing Sheets

ARTICLE IDENTIFICATION DEVICE

FIELD AND BACKGROUND OF THE INVENTION

This invention relates generally to an identification machine for identification of articles and for the identification of the skin of animals or humans and more specifically to a surgical instrument with a reciprocating needle for penetrating the surface of an article to apply ink or the like for identification or cosmetic surgery purposes.

In the past the needle bar of identification machines were attached to the armature of the device by rubber bands or other precarious methods. The needle bars were hard to align and to keep secured. Also, there was no assurance against horizontal movement of the needle bar.

SUMMARY OF THE INVENTION

It is the object of the invention to provide a machine for applying indelible ink to the skin in a precise fashion for medical, veterinary and cosmetic purposes. In the medical area it can be used for marking the effected area of throat cancer while treatment is being done, this thereby indicating the location of the infection and also serving as a indication of the growth of the infection. The machine can also be used by dental surgeons for marking the gums of patients for future surgery. In the cosmetic field it can be used for applying permanent eye liner, permanent lip color or simply skin ornamentation. The veterinary field uses skin markings so as to mark animals for permanent identification to aid in research and animal management.

It is an object of the invention to provide precise application of indelible ink or the like to the skin of a human, animal, or article.

It is another object of the invention to provide a lightweight easy and safe means for applying identifying markings for their various purposes. The machine, in accordance with the invention, with its attachments weighs only 4.6 ounces, has exceptionally good balance, and can be operated with or without a footswitch from a power box or directly from a six volt battery. The machine in accordance with the invention also has a jack plug which is located in the front for connection with a lightweight power supply cord.

It is an object of the invention to provide a needle bar and tube which is easily detachable and secured into place by a locking means preferably including a spring loaded ball and a wing nut, respectively. Also, it is another object of the invention to provide an easily sterilizable needle bar and tube, preferably including a stainless steel needle bar and stainless steel needle tube.

It is still another object of the invention to provide a means to apply identifying markings to objects without horizontal displacement so that better columnation of the needle bar and more precise application of the identification ink is achieved. Accordingly, it is the object of the invention to provide means to achieve this. This is accomplished by the design of the sliding dovetail shaped needle support member or armature and its attachment to the circular rotor and drive unit. This design assures that the needle support member and its attached needle bar will move only vertically and there will be no horizontal displacement thus achieving precise columnation of the needle bar and more precise application of identification ink.

A further object of the invention is to provide an identification device which is simple in design, rugged in construction and economical to manufacture.

For a better understanding of the invention and its operating advantages, reference is made to the accompanying drawings and descriptive matter in which preferred embodiments of the invention are illustrated.

BRIEF DESCRIPTION OF THE DRAWINGS In the drawings.

DESCRIPTION OF PREFERRED EMBODIMENTS

Figure 1:
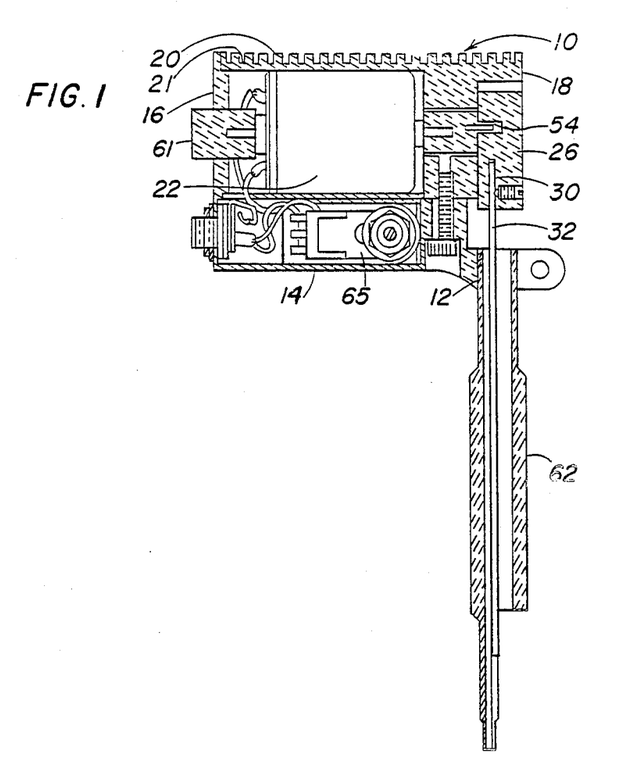
FIG. 1 is a cross section of the right side view of an identification machine according to this invention emphasizing the variable speed control, the lock in needle bar, the spring loaded ball set screw, and the dove tail armature bar.
Figure 4:
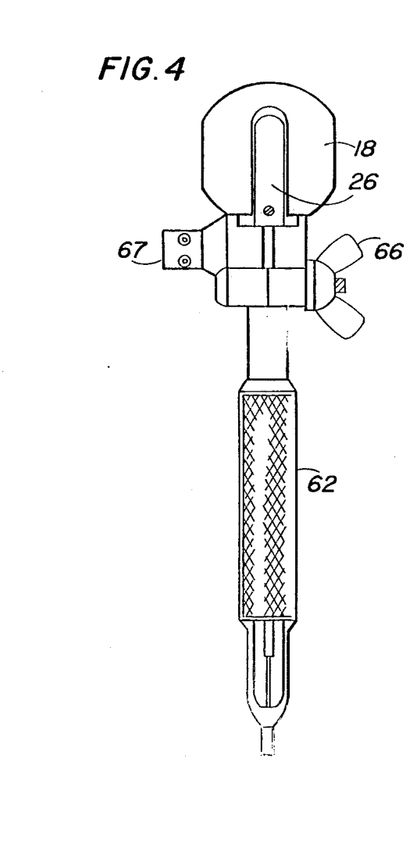
FIG. 4 is a rear view of an identification device according to this invention.
Figure 6:
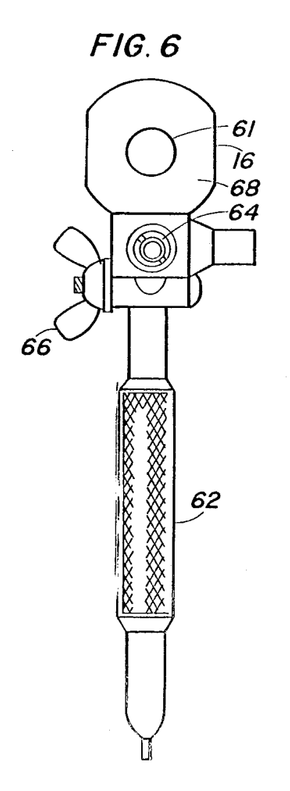
FIG. 6 is a front view of an identification device according to this invention showing the press fit rear housing cap.
Figure 7:
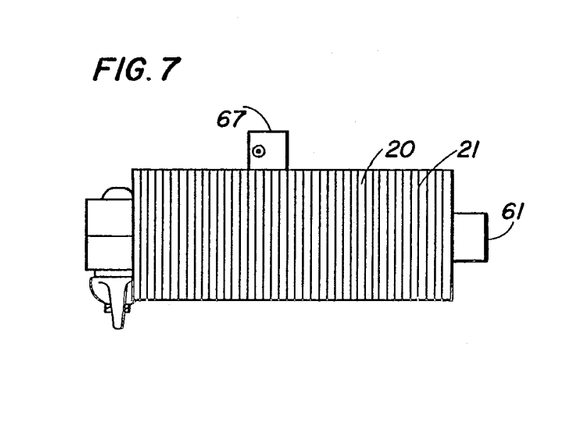
FIG. 7 is a bottom view of an identification machine according to this invention.
Figure 8:
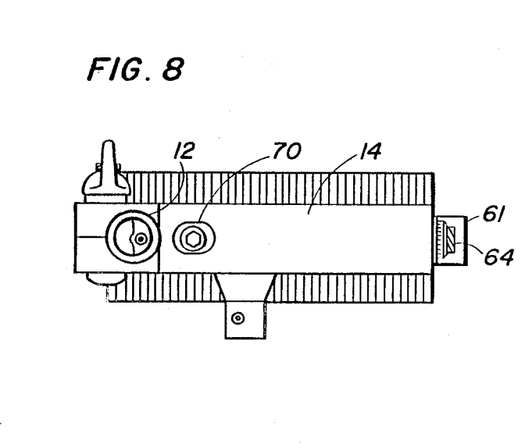
FIG. 8 is a bottom view of an identification machine according to this invention showing the slotted hole for adjustment of the motor housing.

The device according to the invention as seen in FIG. 1 includes a housing, preferably made of DELRIN for lightness and durability, generally designated 10, including a needle guide portion 12 a bottom side portion 14, both of which can be seen in FIG. 8, a front side portion 16, as seen in FIG. 6, a rear portion 18, seen in FIG. 4, and a top portion 20, seen in FIG. 7. Top portion 20 preferably includes fin like members 21 which are adapted to transfer heat to the exterior of the housing. Situated within the housing there is advantageously arranged a motor 22 as seen in FIG. 1 which preferably can run for 300 hours non-stop.

Figure 9:
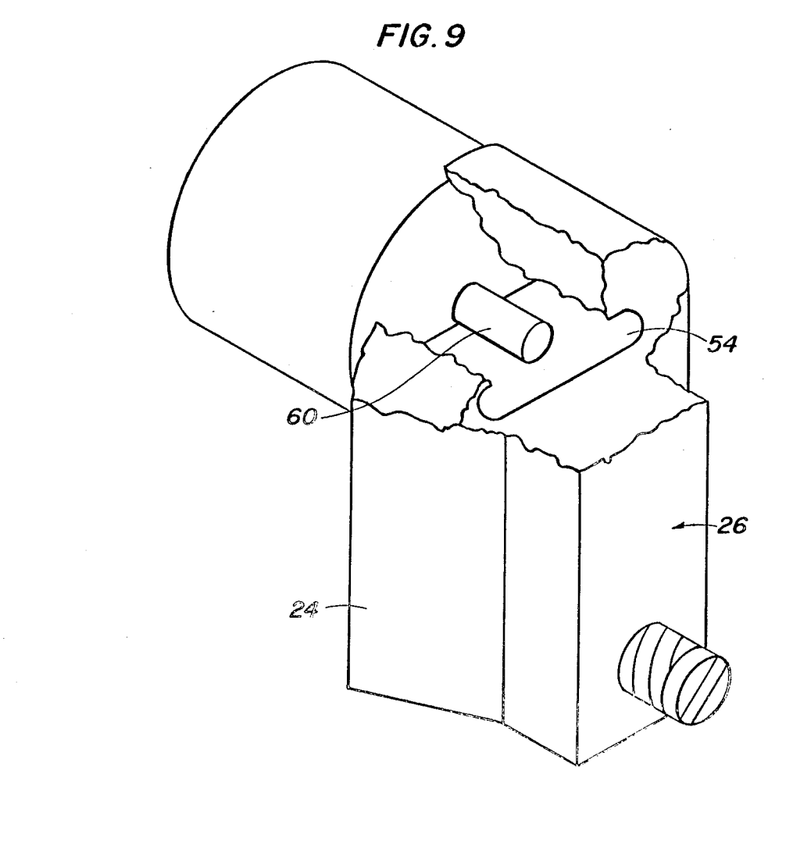
FIG. 9 is an enlarged cutaway view of the dovetail shaped armature according to this invention, showing the horizontal rear slot of the dovetail shaped armature with rotor riding in it.
Figure 13:
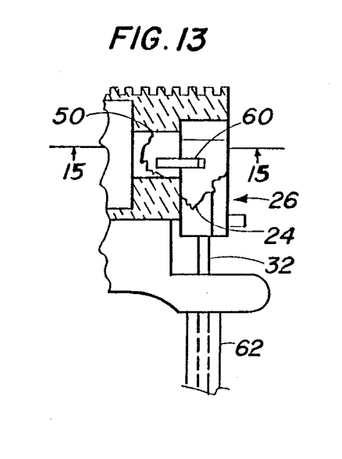
FIG. 13 is a cutaway right side view of an identification device according to this invention showing the rotor and armature in a fully depressed position.
Figure 14:
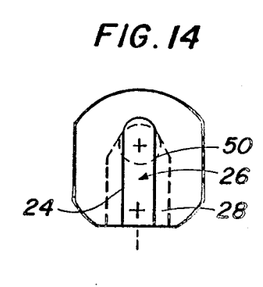
FIG. 14 is a rear view of the body of an identification device according to this invention demonstrating the relationship of the dovetail shaped needle support member or armature with the main body.
Figure 15:
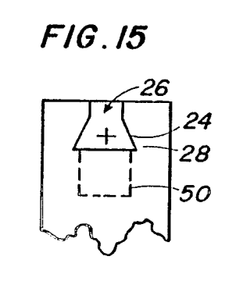
FIG. 15 is a cross section taken from line 15—15 of FIG. 13 depicting the bottom view of an identification device according to this invention and the relationship of the dovetail shaped needle support member and rotor and their placement in the housing of the device.

A needle support member 26 is mounted within the housing for upward and downward reciprocating movement, FIG. 9. The support member or armature 26, preferably includes an engagement member or dovetail portion 24 which is adapted to engage the slotted portion 28 of the housing 10 as best seen in FIGS. 13 and 14.

Figure 2:
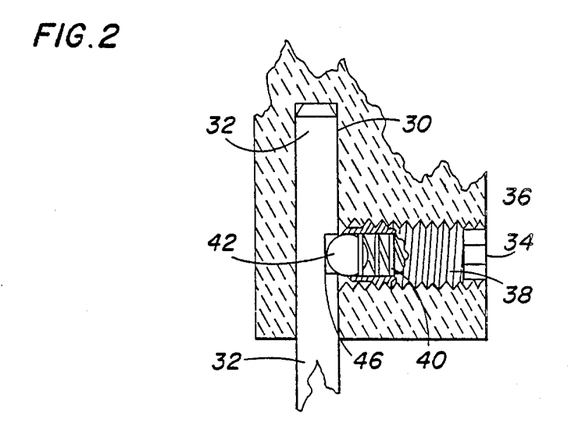
FIG. 2 is a cross section showing the armature bar and needle section detail of an identification device according to this invention.

The needle support member 26 advantageously includes a needle receiving bore 30 for receiving needle bar 32, FIG. 2. The bore 30 is connected to locking means, generally designated 34. Locking means 34 includes a bore 36 having a threaded screw 38 engaging the threaded portion of the bore at the rear face of the needle support member 26. A spring 40 is advantageously placed within the bore 36 and presses at one side against the screw 38. A ball 40, or the like, presses against the spring so as to be biased into the needle receiving portion.

The needle bar 32 preferably includes a notch or bore 46 which is adapted to be engaged by the ball 42 of the locking means. The screw 38 may be adjusted in the threaded bore 36 portion as to increase or decrease the spring force which is applied via the ball 34 on the needle bar 32. When the needle bar 32 is inserted within the needle receiving portion 30 the ball 42 presses against the upper most side of the needle bar 32. As the bore 46 of the needle bar 32 comes into alignment with the bore 36 having the spring 40 and the ball 42 the ball 42 engages the bore 36 of the needle bar 32 so as to lock the needle bar 32 into position. The needle bar 32 may be removed preferably by lessening the spring force by adjusting the screw 38.

A cylindrical shaped tube surrounds the needle bar 32 to act as protection for the needle bar 32 and also as a stationary grip by which to hold the device when applying ink to an article. The tube 62 fitting into the circular needle guide portion 12 of the housing 10, as seen in FIG. 8. The tube secured into place or removed by means of tightening or loosening of a wing nut 66, preferably made of nylon, as seen in FIGS. 5 and 6.

Figure 10:
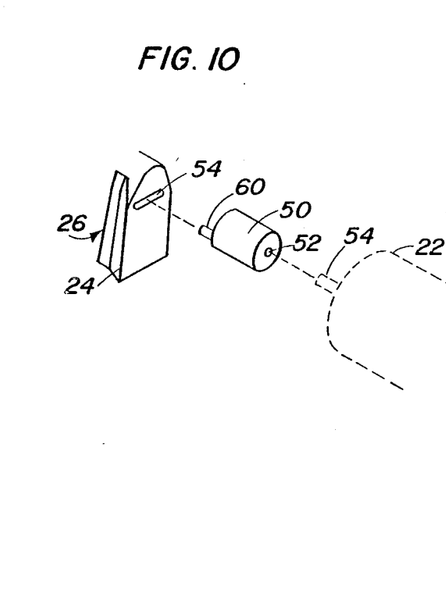
FIG. 10 is an exploded perspective view of assistance in explaining the positional relationships of the dove tail shaped armature, the rotor, and the motor of an identification device according to this invention.

A drive transmission means or rotor 50 is rotatively mounted within the housing 10 by a bore 52. A connecting shaft 54, connects the motor 22 and the rotor 50 as seen in FIG. 10.

Figure 11:
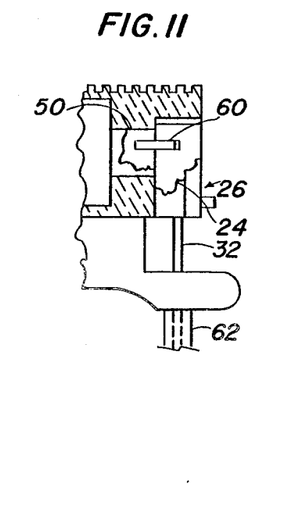
FIG. 11 is a cutaway right side view an identification device according to this invention showing the rotor and armature in a retracted position.
Figure 12:
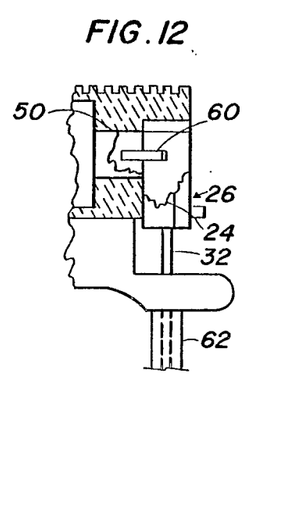
FIG. 12 is a cutaway right side view of an identification device according to this invention showing the rotor and armature in a midway position.

A pin 60 is mounted on the rearward side of the rotor 50 and is offset from the central axis of rotor 50. The pin 60 engages with the needle support member 26 through the slot in the needle support member 54 of FIG. 10. The slot member or horizontal slot membr 54 is advantageously constructed so that upon rotation of the rotor 50 the pin 60 offset from the central axis forces the needle support member 26 to reciprocate as the pin 60 follows a circular motion about and spaced apart from the central axis of the rotor 50. The horizontal slot 54 in the needle support member 26 allows a transmission of the rotational motion into the reciprocating motion of the needle support member 26. Additionally, the advantageous dovetail connection in the slots 28 of the housing 10 allows the dovetail shaped armature or needle support member 26 to slide in the housing 10 as it reciprocates up and down. FIGS. 11 through 13 show the various positions of rotor 50 and needle support member 26 as it reciprocates back and forth.

Figure 3:
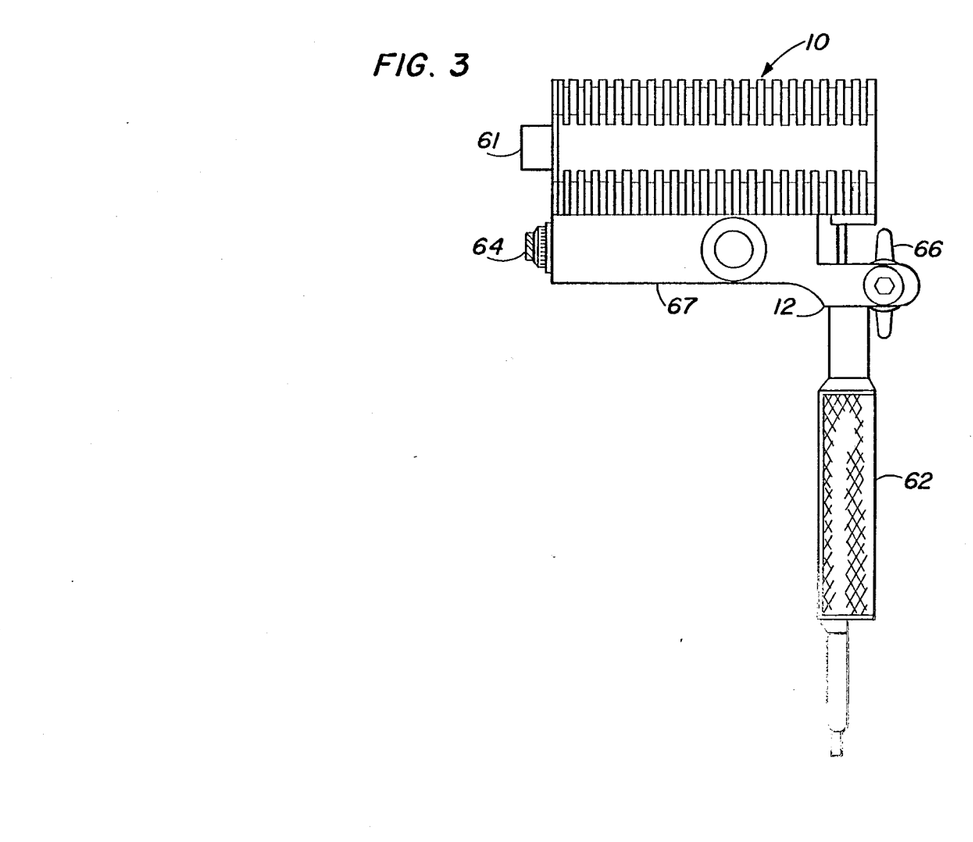
FIG. 3 is a right side view of an identification device according to this invention.
Figure 5:
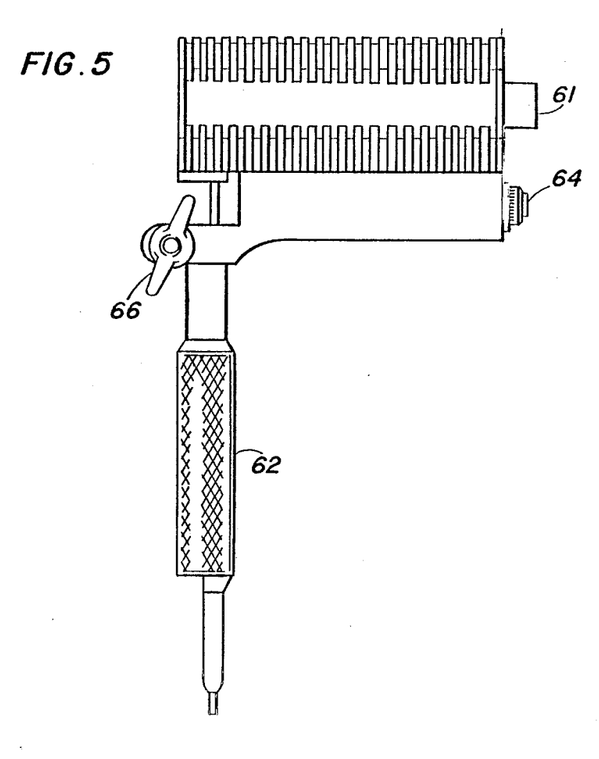
FIG. 5 is a left side view of an identification device according to this invention.

The housing 10 also accommodates a motor shaft knob 61 of FIG. 5 for adjustment of the needle bar 32 when replacing the tube 62 in which the needle bar 32 is housed. A jack plug 64 is positioned below the motor shaft knob 61 on the rear portion of the housing 16 as seen in FIG. 5. A variable speed control 65 is built into the bottom of the machine housing. A speed control knob 67, preferably made of aluminum so as to also act as a heat sink, is located on the right side of the housing 10 as shown in FIG. 3. A press fit cap 68 for sealing the motor 22 is located on the rear portion of the housing 16 as shown in FIG. 6. Lastly, a slotted hole 70 is located on the bottom side portion of the housing 14 for adjustment of the housing 10 to accommodate varying numbers of needles.

As described above, the identification device of this invention makes it possible to use indelible ink either by dipping the needle in ink, having an automatic feed supply ink to the needle, or by a reservoir of ink in the tip of the needle to permanently mark objects or the skin of animals and humans with precision and ease. The identification device according to this invention has no horizontal displacement of the needle bar, all moving parts are self lubricating, and it weighs preferably less than 4.6 ounces with all its attachments.

While a specific embodiment of the invention has been shown and described in detail to illustrate the application of the principles of the invention, it will be understood that the invention may be embodied otherwise without departing from such principles.

What is claimed is:

1. An identification device for applying permanent identification ink to an article comprising:
    a housing having a slotted portion forming a track;
    a motor mounted within said housing;
    a needle support member mounted in said slotted portion of said housing for upward and downward reciprocating movement along said track, said needle support member having a needle receiving portion and having a transmission slot;
    a rotor rotatably mounted in said housing and operatively connected to said motor for rotation about a central axis;
    a connection pin mounted on said rotor and spaced apart from said rotor central axis so as to move in a circular path upon rotation of said rotor, said connection pin extending into said needle support member transmission slot so as to be engageable with said needle support member;
    a needle bar engageable with said needle support member; and,
    locking means connected to said needle support member for connecting and disconnecting said needle bar, said pin member causing said needle support member to reciprocate between an upper and lower position along said track upon circular motion of said pin member as said pin member engages said needle support member in said needle support member transmission slot.

2. An identification device for applying permanent identification ink to an article according to claim 1 wherein the locking means includes a needle receiving bore located on the bottom portion of the needle support member for holding the needle bar, a bore in the rear portion of said needle support member, a spring placed within this said bore that presses against a screw, a ball engaging the other end of said spring, and a notch on the upper section of said needle bar engaging said ball securing the needle bar in place by the alignment of the notch with the ball, the spring, and the screw which can be adjusted to a desired tightness.

3. An identification device according to claim 2 wherein said housing is streamlined in shape and includes fins for dissipating heat.

4. An identification device according to claim 2 further comprising a variable speed control built into the bottom of said housing for the purpose of regulating the speed of the machine.

5. An identification device according to claim 4 wherein said speed control includes a speed control knob located on the side of the housing to control the speed of the motor and to also act as a heat sink.

6. An identification device according to claim 2 wherein said tube is etched with a cross-hatch design to allow gripping of the device without slippage when applying ink onto an object.

7. An identification device according to claim 2 wherein a knob is provided on said housing to allow turning of the motor shaft for adjusting said needle bar when replacing said tube.

8. An identification device according to claim 2 wherein a jack plug is positioned on the side of said housing for connecting the device to a power source.

9. An identification device for applying permanent identification ink to the skin or an object, comprising:
   a housing;
   a motor mounted within said housing;
   a sliding dovetail-shaped armature needle support member contained in an end of said housing;
   a needle bar snap fitted into said support member in a fixed position;
   a tube housing said needle bar;
   a horizontal slot at the rear of said support member;
   a circular rotor connecting said support member to said motor.

10. An identification device for applying permanent identification ink to the skin or an object, according to claim 9 further comprising: a motor housing attached to said housing for supporting said motor and means for adjusting the position of said motor housing and said motor relative to said housing.

11. An identification device for applying permanent identification ink to the skin or an object, according to claim 10 wherein: the width of said needlebar tube is as large as the distance said motor may be adjusted so as to allow a plurality of needles to be connected to said needle bar.

12. An identification device for applying permanent identification ink to the skin or an object, according to claim 10 further comprising: a slotted hole on the bottom of the housing for access to said means for adjusting the position of said housing.

13. An identification device for applying permanent identification ink to the skin or an object, according to claim 9 further comprising: means to vary speed of said motor; knob control means, connected to said means to vary the motor; and a press fit cap closing an opening of said housing.

14. An identification device according to claim 13 whereby said press fit cap is located at the front portion of the housing for sealing the motor and allowing accessability to the motor.

15. An identification device according to claim 9 wherein said tube surrounds said needle bar and is tightened into place by a wing nut that also allows for easy release of said tube.

16. An identification device according to claim 9 wherein said tube surrounds said needle bar for protection of said needle bar.

17. An identification device according to claim 9 wherein the said needle bar locked into the bottom of said needle support member holds needles used in the application of identification ink.

18. An identification device for applying permanent identification ink to an article comprising:
   a housing;
   a motor mounted within said housing;
   a needle support member mounted in said housing for upward and downward reciprocating movement and having a needle receiving portion;
   a drive transmission means connected between said motor and said needle support member for providing reciprocating motion to said needle support member;
   a needle bar engageable with said needle support member; and,
   locking means connected to said needle support member for connecting and disconnecting said needle bar,
   the locking means including a needle receiving bore located on the bottom portion of the needle support member for holding the needle bar, a bore in the rear portion of said needle support member, a spring placed within this said bore that presses against a screw, a ball engaging the other end of said spring, and a notch on the upper section of said needle bar engaging said ball securing the needle bar in place by the alignment of the notch with the ball, the spring, and the screw which can be adjusted to a desired tightness,
   said housing can be adjusted forwards or backwards for accommodating a varying number of needles by adjusting an adjustment member connected to said motor housing and adjustably connected through a slotted hole on the bottom portion of the housing.

* * * * *